United States Patent [19]

Raspanti et al.

[11] Patent Number: 5,639,446
[45] Date of Patent: Jun. 17, 1997

[54] DERIVATIVES OF BENZOXAZOLE USEFUL AS UV STABILIZERS

[75] Inventors: Giuseppe Raspanti; Giorgio Zanchi, both of Bergamo, Italy

[73] Assignee: 3V Inc., Weehawken, N.J.

[21] Appl. No.: 710,776

[22] Filed: Sep. 20, 1996

[51] Int. Cl.$^6$ .......................... A61K 7/42; C07D 413/12; C07D 263/57

[52] U.S. Cl. .......................... 424/59; 514/321; 514/375; 514/844; 546/198; 546/224; 524/94

[58] Field of Search .......................... 546/198; 548/224; 514/321, 375; 424/59, 60; 524/94

[56] References Cited

U.S. PATENT DOCUMENTS

| | | | |
|---|---|---|---|
| 4,062,800 | 12/1977 | Irick | 252/402 |
| 4,182,703 | 1/1980 | Irick | 260/45.8 RW |

*Primary Examiner*—C. Warren Ivy
*Assistant Examiner*—Evelyn Huang
*Attorney, Agent, or Firm*—Griffin, Butler, Whisenhunt & Kurtossy

[57] ABSTRACT

Compounds of formula (I)

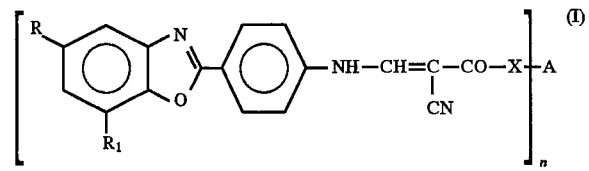

wherein the groups are as defined in the description, are useful as sunscreens in cosmetics and in the stabilization of synthetic polymers.

13 Claims, No Drawings

DERIVATIVES OF BENZOXAZOLE USEFUL AS UV STABILIZERS

The present invention relates to derivatives of the benzoxazole, their use in cosmetic compositions and in the stabilization of synthetic polymers.

BACKGROUND OF THE INVENTION

It is well known that sun radiations ranging from 290 to 400 nm are noxious for the organic materials, among which cutaneous tissue too. In fact, prolonged exposition to sun radiation is considered to be the main cause of the development of degenerative processes and of skin cancer forms. In particular, radiations of wavelength between 290 and 320 nm, so called UV-B radiations, cause erythema and sunburns, whose severity depends on exposure length.

It was ascertained that also the radiations ranging between 320 and 400 nm, so called UV-A, and responsible of skin tanning, can cause alterations and damages in the skin which may not be disregarded, such as for example degenerative processes and even cancer forms; especially in case of sensible skins or in case of prolonged exposition to radiation.

It has also been demonstrated that the UV-A radiation other than causing damages to elastin and collagen, whose consequence is ageing of the skin, can also be the cause of a number of phototoxic and photoallergic reactions. Beside, the noxious action of UV-B may be enhanced by the presence of UV-A (see: Willis et al.: Journal of Investigative Dermatology vol. 59, 416, 1072).

By means of the use of particular compounds or of compositions containing these particular compounds, so called sunscreens, capable of absorbing, at least partially, UV sunlight radiations, noxious effects on organic materials, in particular on synthetic polymers and on human skin can be prevented or at least attenuated and ageing of the same slowed down. As protective agents a number of substances have been studied and experimented and a wide patent literature exists on this matter, in which compounds belonging to different chemical classes capable of absorbing in the UV zone of sun radiation and particularly that between 290 and 360 nm are proposed.

Many compounds, such as for example derivatives of cinnamic acid, 4-aminobenzoic acid, benzylydenecamphor, benzophenone, and diphenylcyanoacrylic acid are well known and widely used in cosmetic preparations for the protection from sunburns and erythema due to noxious UV-B radiation.

Until recently, the use of sunscreens for the protection from the UV-A radiation was practically unknown, other than some special cases of therapy. But recent studies show that also a continuous and intensive UV-A radiation can cause severe cutaneous damages, especially to persons having very sensitive and delicate skin.

For the protection against UV-A, really suitable products are not yet available, even if in the patent literature some compounds have been proposed, but in practice, the outcome of these compounds may not be considered sufficiently positive.

2-hydroxy-4-methoxybenzophenone is an often used commercial product, whose maximum absorption in the UV-A zone at about 325 nm, is too low to give an effective protection and, moreover its solubility in solvents usually used in cosmetics is very low thus making difficult its handling.

Another compound actually used in practice is a dibenzoylmethane derivative, but not only it is incompatible with many ingredients usually employed for cosmetic compositions, but also has the severe defect of not being sufficiently photostable (Int. J. Cosm. Science 10, 53 1988) the sun formulations containing these compounds may not guarantee a sufficient protection from UV-A since the sunscreens are either too weak (such as the benzophenone derivative) or are degraded too quickly by the radiation itself (such as the dibenzoylmethane derivative).

To date, therefore, it is not possible to satisfy the market requirements, since industry has not yet made available sunscreens capable of providing a sufficient protection from sunlight UV-A radiations.

DISCLOSURE OF THE INVENTION

It has now surprisingly been found that particular derivatives of benzoxazole have such characteristics to meet the present market requirements. In fact, in addition to absorption, a high protective efficiency in the zone between 320 and 360 nm, is provided and they also show good photostability and wide compatibility with the ingredients usually employed in cosmetic compositions.

The compounds according to the present invention have the following formula (I):

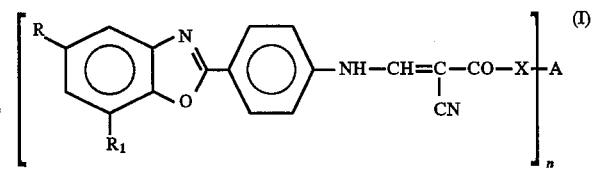

in which

R and $R^1$, which can be the same or different, are hydrogen, linear or branched $C_1$–$C_8$ alkyl; -$OR_2$ wherein $R_2$ is a $C_1$–$C_4$ alkyl; -$COOR_3$ wherein $R_3$ is linear or branched $C_1$–$C_{20}$ alkyl, $C_5$–$C_8$ cycloalkyl; or a group of formula (II) or (III):

in which

B is linear or branched $C_1$–$C_8$ alkyl; $C_5$–$C_8$ cycloalkyl; phenyl, optionally substituted with one or more $C_1$–$C_4$ alkyl; $R_4$ and $R_5$ are independently hydrogen or methyl, m can have values from 1 to 10;

n can be the number 1 or 2,

A, when n is 1, represents linear or branched $C_1$–$C_{24}$ alkyl or a group of formula (II) or (III), A, when n is 2 is $C_2$–$C_{12}$ alkylene or the group of formula (IV):

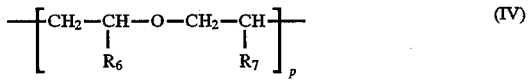

in which $R_6$ and $R_7$, which can be the same or different, are hydrogen or methyl, p has the same definition of m;

X is oxygen or NH.

A first group of preferred compounds comprises those wherein R, $R_1$, A and n have the above defined meaning and X is oxygen.

A second group of preferred compounds comprises those wherein R, $R_1$, A and X have the above defined meaning and n is 1. Examples of alkyl are methyl, propyl, butyl, hexyl, heptyl, octyl, decyl, dodecyl, pentadecyl, heptadecyl, eicosanyl and their branched isomers, optionally containing oxygen bridges in the form of ether groups. Particularly preferred are the groups 2-octyldodecyl, 2-ethyldecyl, terbutyl, 2-ethylhexyl, 1,1,3,3-tetramethylbutyl, isobutyl.

Examples of substituted phenyls are tolyl, ethylphenyl, propylphenyl, butylphenyl.

Examples of cycloalkyl are cyclopentyl, cyclohexyl, cyclooctyl.

The compounds according to the present invention absorb UV radiations intensely and particularly in the UV-A range, therefore small amounts of these compounds are sufficient to obtain cosmetic compositions with high SPF (Sun Protecting factor). SPF is directly related to the specific estinction and is determined in vivo on man or according to a in vitro method as described by B. Diffey J. Robson in J. Soc. Cosmet. Chem. 40, 127–133 (1989).

It is therefore a further object of the invention the use of the compounds of formula (I) as sunscreens in cosmetic compositions and as photostabilizing agents for the protection of synthetic polymers.

In particular, it is an object of the present invention a method for protecting human skin from sunlight radiations consisting in applying on the human skin an effective amount as sunscreen of a compound of formula (I), suitably formulated in a cosmetic composition in admixture with conventional vehicle and excipients.

Another object of the present invention are cosmetic compositions containing at least a compound of formula (I).

The compounds according to the present invention can be prepared by reacting a compound of formula (V):

$$[NC-CH_2-CO-X]_n-A \qquad (V)$$

wherein X, A and n are as above defined, with at least n equivalents of trimethyl- or triethylorthoformate and at least n equivalents of a a compound of formula (VI):

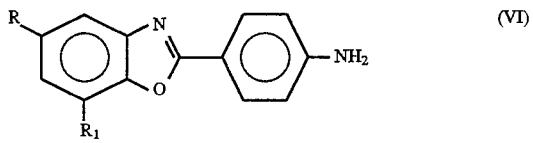

wherein R and $R_1$ are as above defined.

The reaction is carried out at a temperature ranging between 50° and 200° C., preferably between 100° and 150° C., in a polar organic solvent, such as for example n-propyl alcohol, n-butyl alcohol, isobutyl alcohol or ethylene glycol, diethylene glycol, propylene glycol, ethylene glycol monomethyl- or dimethyl ether. The final compounds are isolated and purified according to usual methods.

In a different embodiment of the present application, where in a compound of formula (I), n is the integer 2, or when n is the integer 1 and A is different from methyl or ethyl, the preparation of the compounds can be carried out by reacting a compound of formula (VII)

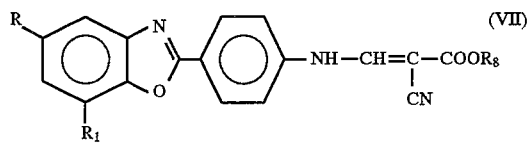

wherein R and $R_1$ have the above meanings and $R_8$ is methyl or ethyl, with a compound of formula (VIII):

$$A(XH)_n \qquad (VIII)$$

wherein A, X and n have the above meaning.

In this case, the reaction is preferably carried out in the presence of a transesterification catalyst, such as for example a tetraalkyl titanate or a sodium or potassium alcoholate in an apolar solvent, such as toluene or xylene or even in the absence of any solvent.

According to the present invention, the compounds of formula (I) are useful as sunscreens. Their protective activity on the skin from sun radiation is carried out by applying a suitable amount on the part of the skin which is exposed to the radiations.

Suitable amounts for the applications can be determined by the skilled person in the art depending on the specific estinction coefficient $E_1^1$ of the compound of formula (I). Said coefficient is an index of the protection efficacy.

A further object of the present invention is represented by cosmetic compositions containing an effective amount of at least a compound of formula (I) as sunscreen in combination with conventional vehicles and excipients. Said compositions can be of different types, for example in the form of solutions, lotions, water-in-oil or oil-in-water emulsions; or also in the form of gels, lipsticks, aerosols.

The compositions according to the present invention can be prepared by admixing conventional ingredients, vehicles and excipients such as oils, fats, emollients, hydrating agents, moisturizing agents, softening agents, preservatives, surfactants, thickening agents, antifoam, perfumes, pigments, dyes and other else such as alcohols, polyols, electrolytes, silicone derivatives. The most commonly used solvents are triglycerides of caprinic or caprilic acid, castor oil, esters of fatty acids with isopropanol, propylene glycol, glycerin, propylene glycole-monomethyl or monoethyl or monobutyl ether.

The present invention also comprises a method for protecting cosmetics from UV radiation by adding a sufficient amount of the compounds of formula (I). In this case it is the composition whose ingredients can undergo unwanted degradation or colouring due to light to be protected from radiation induced-degradation. Such a composition may be for example hair shampoos and lacquers, hairdress lotions, hair-dye compositions, formulations for make-up, such as nail lacquers, foundation and lipstick. Preferred cosmetic compositions are those for the protection of human skin from sun radiations. A skilled person shall be able to determine the sufficient amount of compound of formula (I) to add to a cosmetic composition in order to protect it from photodegradation.

For the purpose of protecting human skin from sunburns, the cosmetic compositions according to the present invention can contain one or more compounds of formula (I), in an amount comprised from 0.1 to 20%, preferably from 0.5 to 15% by weight with respect to the total weight of the composition.

Other than compounds of formula (I), the claimed compositions can contain in combination also any other sunscreens and particularly those having a maximum absorption comprised from 290 to 320 nm.

In such a manner, a protection both towards UV-A and UV-B radiations can be obtained.

Well known sunscreens, which can be combined with the compounds of formula (I) are for example: 3-(4-methylbenzylydene)-camphor; 2-ethylhexyl-(4-dimethylamino)benzoate, 2-ethylhexyl-4-methoxy-cinnamate, menthyl salicylate, 2-hydroxy-4-methoxy-benzophenone, 2,4,6-tri-anilino-(p-carbo-2-ethylhexyloxy)-1,3,5-triazine, 4-(1,1-dimethylethyl)-4'-methoxydibenzoylmethane, triazine derivatives disclosed in EP 0570838, 2-ethylhexyl-2-cyano-3,3-diphenyl acrylate, salts of 2-phenyl-benzimidazol-5-sulfonic acid or of 2-hydroxy-4-methoxy-benzophenone-5-sulfonic acid. The application of sunscreens according to the present invention can be carried out by means of cosmetic compositions containing one or more compounds of formula (I), optionally combined with one or more well-known sunscreens, such as those above cited.

It is understood that the above list of sunscreens which may be combined with the sunscreens of formula (I) is not intended to be limited, but may be expanded by the skilled person.

The cosmetic compositions according to the present invention may contain also inorganic pigments, commonly used in cosmetics, such as for example those used for the protection of human skin from UV radiations, for example titanium, zinc, silicon or aluminium oxides.

In another aspect, the present invention also provides a method for stabilizing a synthetic polymer against sunlight induced-degradation comprising adding an effective amount of at least a compound of formula (I), optionally in combination with other well-known stabilizing agents and additives for polymers.

According to the present invention as a polymeric material, which can be protected from UV radiation, it is intended polyethylene, polypropylene, polystyrene, polybutadiene, polyisoprene and their copolymers, polyvinyl acetate and its copolymers, particularly with polyethylene, polyesters such as polyethylene terephthalate, polyamides such as Nylon 6 and Nylon 6,6, polyurethanes, polyacrylates, polymethacrylates, polyvinyl chloride.

The compounds of formula (I) can be incorporated in polymers to be stabilized by means of any known method for mixing or blending additives to polymeric materials; for example, they can be mixed with the polymer in a suitable blender or mixer, or added in the form of solution or suspension in a suitable solvent such as methanol, ethanol, acetone, chloroform, then removing the solvent after mixing with the polymer, which can be in the form of powder, granulate or suspension or finally can be added to the polymer during the preparation of the same, for example in the last step of preparation.

The compounds of formula (I) can be also used in combination with other stabilizing agents and additives generally used for polymers, such as for example phenol-based antioxydants, phosphites, hindered amines and particularly those containing in their structure the 2,2,6,6-tetramethylpiperidine group, other types of UV-absorbers based on benzotriazoles or benzophenones, plastifiers, lubricants, antistatic agents, flame retardants, titanium oxide.

The amount of compounds of formula (I) necessary to an effective stabilization of the polymer depends on different factors, such as the kind and the characteristics of the polymer, the use to which it is intended, the intensity of the radiation, the duration of exposure and the presence, if any, of other stabilizing agents.

Generally, an amount comprised from 0.01 to 5% by weight of the polymer, preferably from 0.05 to 2% is sufficient, but it is understood that a skilled technician in the field shall be able to find a suitable amount.

The following examples further illustrate the invention.

EXAMPLE 1

185.5 g of p-nitrobenzoyl chloride were added to 109 g o-aminophenol in 1,000 ml of xylene.

The so obtained suspension was slowly warmed up to 130° C. Developing hydrochloric acid was neutralized sending it to a NaOH solution.

After HCl development finished (after about 1 hour), 9.5 g of p-toluenesulfonic acid were added to the reaction mixture and stirring was continued at reflux for about 3 hours, while azeotropically distilling and collecting reaction water. After cooling at 60° C., filtering, several washings with acetone and drying, 225 g of 2-(p-nitrophenyl) benzoxazole were obtained in the form of a creamish coloured substance. This substance was loaded together with 1,400 ml of ethylene glycol monomethylether and 2 g of 5% Pt/C in autoclave, washed 2–3 times with nitrogen then with hydrogen.

Subsequently, hydrogen was introduced to reach a pressure of 10 atm and the temperature was slowly raised to 90° C. while stirring. Stirring was continued at 80°–90° C. until the absorption of hydrogen had ceased, keeping the pressure between 10 and 15 atm.

After cooling, the overpressure was discharged, the reaction mixture was washed with nitrogen.

The catalyst was filtered off from the solution, which was then vacuum-evaporated to dryness. The residue was crystallized from toluene with addition of decolouring earth. 170 g of 2-(p-aminophenyl)benzoxazole with m.p. of 176°–179° C. were obtained.

EXAMPLES 2–4

Similarly to the procedure described in Example 1 the benzoxazoles of formula (VI) listed in Table 1 below were prepared.

TABLE 1

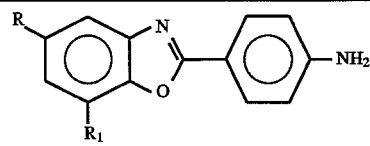

(VI)

| Example | R | $R_1$ | m.p. °C. |
|---|---|---|---|
| 2 | $CH_3$— | H | 191–193 |
| 3 | $(CH_3)_3C$— | H | 167–168 |
| 4 | $C_4H_9$—CH—$CH_2$OOC—<br>\|<br>$C_2H_5$ | H | 91–93 |

EXAMPLE 5

A mixture consisting of 18.9 g of ethyl cyanoacetate, 39.9 g of the compound of Example 3, 24.9 g of triethyl orthoformate in 250 ml of ethylene glycole, was slowly warmed up to 150° C., while distilling the generated ethyl alcohol and stirring for 3 hours. The reaction mixture was cooled to 60° C., 300 ml of methanol were added, cooling was carried to 20° C. and the precipitate was filtered.

The panel was washed several times with methanol and, after drying, it was crystallized from acetone. The compound of the following formula was obtained with m.p. of 183°–184° C. and $E_1^1$ of 1622 at 352 nm.

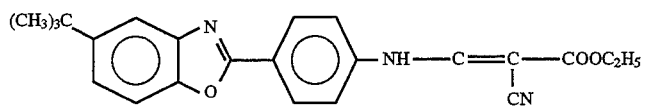

EXAMPLE 6

9.73 g of the compound of Example 5 and 2.18 g of 1,10-decandiol were added to 100 ml of xylene. 0.4 ml of tetrabutyl orthotitanate were added to the mixture and it was slowly warmed up to 170°–180° C. while distilling xylene and the formed ethyl alcohol and stirring for 3 hours.

The residue was crystallized from xylene adding decolouring earth.

The compound of the following formula was obtained with m.p. of 207°–209° C. and $E_1^1$ of 1434 at 352 nm.

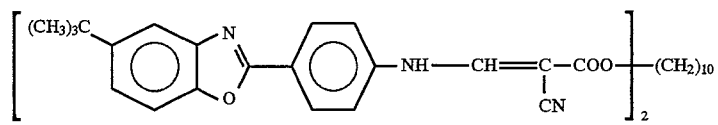

EXAMPLES 7–13

In a similar manner as in Example 1 or 2, starting from the compounds of Examples 1–5, the compounds of formula (Ia) listed in Table 2 below were prepared.

TABLE 2

| Example | R | A | X | M.P. °C. | $E_1^1$ | nm |
|---|---|---|---|---|---|---|
| 7 | $(CH_3)_3C-$ | $C_4H_9-CH(C_2H_5)-CH_2OOC-$ | O | 124–126 | 1.344 | 353 |
| 8 | H | $C_2H_5$ | O | 238–240 | 1.834 | 351 |
| 9 | H | $C_{10}H_{21}-CH(C_8H_{17})-CH_2-$ | O | 103–104 | 1.085 | 351 |
| 10 | $C_4H_9-CH(C_2H_5)-CH_2OOC-$ | $C_2H_5$ | O | 200–201 | 1.376 | 352 |
| 11 | $(CH_3)_3C-$ | 2,2,6,6-tetramethylpiperidin-4-yl (HN ring with CH₃, CH₃, CH₃, CH₃) | O | 212–215 | 1.244 | 353 |
| 12 | $(CH_3)_3C-$ | $C_4H_9-O-CH_2-CH_2-O-CH_2-CH_2-$ | O | 144–146 | 1.253 | 352 |

TABLE 2-continued

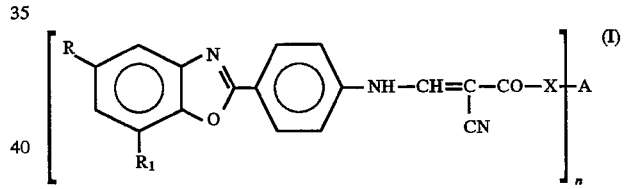

| Example | R | A | X | M.P. °C. | $E_1^1$ | nm |
|---|---|---|---|---|---|---|
| 13 | $(CH_3)_3C-$ | $C_4H_9-CH-CH_2OOC-$<br>$\quad\quad\quad\, \|$<br>$\quad\quad\quad C_2H_5$ | NH | 160-162 | 1.394 | 356 |

Example A - Alcoholic gel

| | |
|---|---|
| Propylene glycol | 25.0 g |
| Ethyl alcohol | 25.0 g |
| Synthalen M (thickening agent by 3V-SIGMA) | 0.6 g |
| Compound of Example 6 | 2.0 g |
| Triethanolamine | 0.3 g |
| Abiol (Preservative of 3V SIGMA) | 0.3 g |
| Perfume | 0.3 g |
| Distilled water q.s. | 100 g |

Synthalen M was dispersed in water, then triethanolamine, propylene glycole and ethanol wherein the compound of Example 6 was previously dissolved were added. Perfume was last added.

Example B - Sun-milk

| | |
|---|---|
| Fatty acid Triglycerides | 20.0 g |
| Cetylstearyl alcohol | 2.0 g |
| Lanoline | 4.0 g |
| Cetyl alcohol | 2.0 g |
| Siliconic oil | 0.4 g |
| 2-ethylhexyl-4-dimethylaminobenzoate | 2.5 g |
| Compound of Example 7 | 2.0 g |
| Abiol (preservative by 3V SIGMA) | 0.2 g |
| Synthalen M (thickening agent by 3V-SIGMA) | 0.1 g |
| Triethanolamine | 0.15 g |
| Perfume | 0.3 g |
| Distilled water q.s. | 100 g. |

The fatty phase was heated to 80°–90° C., the compound of example was added, then the mixture was added to water containing the hydrosoluble compounds, heated to 80°–90° C. Warm stirring was continued for 15–20 minutes. After cooling, perfume was added.

Example C - Day-cream

| | |
|---|---|
| $C_8-C_{12}$ acid triglycerides | 29.0 g |
| Glycerol Monostearate | 7.0 g |
| Stearic Acid | 2.0 g |
| Lanoline | 4.0 g |
| Preservative | 0.2 g |
| Compound of Example 10 | 2.5 g |
| Propylene glycole | 2.5 g |
| Triethanolamine | 0.5 g |
| Perfume | 0.3 g |
| Distilled water q.s. | 100 g. |

The composition was prepared as described in Example B.

Example D 1000 g of low density polyethylene (Riblene EF 2100 R Enichem), 2 g of n-octadecyl-3-(3,5-di-terbutyl-4-hydroxyphenyl) propionate, 1 g of calcium stearate and 0.3 g of a compound of formula (I) were homogeneously mixed. The obtained mixtures were extruded at 190° C. and transformed into granules. From these, by pressing at 200° C., films of 0.2 mm were obtained.

Samples of these films were subjected to UV radiations in a Weatheromether WOM Ci-65 at a black panel temperature of 63° C. In the irradiated samples the increase of the carbonylic band at 5.85 nm in infrared field was measured and T-0.1, i.e. the time necessary to achieve an increase of 0.1 of the carbonylic band was determined and compared with a film which did not contain stabilizing agents of formula (I). The results are reported in the Table 3.

TABLE 3

| Stabilizing agent | T 0.1 (Hours) |
|---|---|
| No agent | 360 |
| Compound of Example 7 | 1070 |
| Compound of Example 11 | 1350. |

We claim:

1. A compound of formula (I):

in which

R and $R_1$, which can be the same or different, are hydrogen, linear or branched $C_1-C_8$ alkyl; $-OR_2$ wherein $R_2$ is a $C_1-C_4$ alkyl; $-COOR_3$ wherein $R_3$ is linear or branched $C_1-C_{20}$ alkyl, $C_5-C_8$ cycloalkyl; or a group of formula (II) or (III):

in which

B is linear or branched $C_1-C_8$ alkyl; $C_5-C_8$ cycloalkyl; and phenyl, or phenyl substituted with one or more $C_1-C_4$ alkyl; $R_4$ and $R_5$ are independently hydrogen or methyl, m can have values from 1 to 10;

n can be the number 1 or 2,

A, when n is 1, represents linear or branched $C_1-C_{24}$ alkyl or a group of formula (II) or (III), A, when n is 2 is $C_2$–$C_{12}$ alkylene or the group of formula (IV):

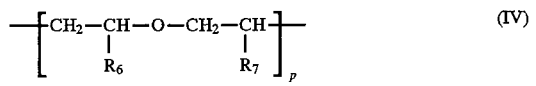

in which $R_6$ and $R_7$, which can be the same or different, are hydrogen or methyl, p has the same definition of m; X is oxygen or NH.

2. A compound according to claim 1, wherein X is oxygen.

3. A compound according to claim 1, wherein n is 1.

4. A method for protecting human skin from sunlight radiations comprising in applying on the human skin an effective amount as sunscreen of a compound of claim 1, formulated in a cosmetic composition.

5. A method for protecting a cosmetic composition from sunlight UV radiation-induced degradation, comprising incorporating in said composition an effective amount of a compound of claim 1.

6. A cosmetic or dermatologic composition comprising one or more compounds of claim 1 in amount from 0.1 to 20% by weight with respect to the composition.

7. A cosmetic or dermatologic composition according to claim 6, containing an additional sunscreen.

8. A composition according to claim 7, wherein said additional sunscreen is selected from the group consisting of 3-(4-methylbenzylydene)-camphor; 2-ethyl-hexyl-(4-dimethylamino)benzoate, 2-ethylhexyl-4-methoxy-cinnamate, menthyl salicylate, 2-hydroxy-4-methoxy-benzophenone, 2,4,6-tri-anilino-(p-carbo-2-ethylhexyloxy)-1,3,5-triazine, 4-(1,1-dimethylethyl)-4'-methoxydibenzoylmethane, 2-ethylhexyl-2-cyano-3,3-diphenyl acrylate, salts of 2-phenyl-benzimidazol-5-sulfonic acid or of 2-hydroxy-4-methoxy-benzophenone-5-sulfonic acid.

9. A composition according to claim 6, further containing inorganic pigments.

10. A method for stabilizing a synthetic polymer against sunlight induced-degradation comprising adding an to the polymer effective amount of at least one compound of claim 1.

11. Compositions of synthetic polymers comprising the polymers and 0.05–5% by weight with respect to the polymers of a compound of claim 1.

12. A method according to claim 10, wherein additional stabilizing agents and additives are added to the polymer.

13. A composition according to claim 11, wherein the composition also contains additional stabilizing agents or additives for the polymer.

* * * * *